US010391040B1

(12) United States Patent
Schutt et al.

(10) Patent No.: US 10,391,040 B1
(45) Date of Patent: Aug. 27, 2019

(54) ORTHODONTIC MATERIAL, DEVICE AND METHODS OF PRODUCING THE SAME

(71) Applicant: OrVance, LLC, Caledonia, MI (US)

(72) Inventors: Ronald J. Schutt, Grand Rapids, MI (US); Michael Edward Silver, Holland, MI (US)

(73) Assignee: ORVANCE, LLC, Caledonia, MI (US)

( * ) Notice: Subject to any disclaimer, the term of this patent is extended or adjusted under 35 U.S.C. 154(b) by 0 days.

(21) Appl. No.: 15/582,270

(22) Filed: Apr. 28, 2017

Related U.S. Application Data

(60) Provisional application No. 62/328,973, filed on Apr. 28, 2016.

(51) Int. Cl.
A61K 6/093 (2006.01)
A61K 6/083 (2006.01)
A61K 6/027 (2006.01)
A61Q 11/00 (2006.01)
A61K 8/24 (2006.01)
A61K 8/21 (2006.01)
A61K 8/23 (2006.01)
A61C 7/14 (2006.01)

(52) U.S. Cl.
CPC ............. A61K 6/093 (2013.01); A61C 7/14 (2013.01); A61K 6/027 (2013.01); A61K 6/083 (2013.01); A61K 8/21 (2013.01); A61K 8/23 (2013.01); A61K 8/24 (2013.01); A61Q 11/00 (2013.01); A61K 2800/592 (2013.01)

(58) Field of Classification Search
None
See application file for complete search history.

(56) References Cited

U.S. PATENT DOCUMENTS

| 3,455,872 A | 7/1969 | Beck |
| 4,497,926 A | 2/1985 | Toy |
| 5,624,745 A | 4/1997 | Lapidus |
| 6,638,881 B2 | 10/2003 | Lapidus |
| 7,195,484 B1 | 3/2007 | Wagner |
| 7,312,256 B2 | 12/2007 | Borja |
| 7,789,662 B2 | 9/2010 | Van Eikeren et al. |
| 8,007,277 B2 | 8/2011 | Fischer |
| 2003/0205234 A1 | 11/2003 | Bardach |
| 2005/0089820 A1* | 4/2005 | Allred ............. A61C 5/00 433/215 |
| 2005/0181324 A1 | 8/2005 | Hare |
| 2005/0239015 A1 | 10/2005 | Dragan |
| 2006/0063128 A1 | 3/2006 | Dragan |
| 2007/0185237 A1 | 8/2007 | Rajaiah et al. |
| 2008/0293015 A1 | 11/2008 | Wong et al. |
| 2012/0107768 A1 | 5/2012 | Diedwardo |
| 2012/0199138 A1 | 8/2012 | Hannapel |
| 2014/0017637 A1 | 1/2014 | Cinader, Jr. et al. |
| 2015/0037266 A1 | 2/2015 | Boyd et al. |
| 2015/0209120 A1* | 7/2015 | Hannapel ............ A61C 7/125 433/2 |

FOREIGN PATENT DOCUMENTS

| CA | 2858830 A1 | 6/2013 |
| EP | 2544651 A1 | 1/2013 |
| WO | 2011112193 A1 | 9/2011 |

* cited by examiner

Primary Examiner — Brian Gulledge
(74) Attorney, Agent, or Firm — Nyemaster Goode, P.C.

(57) ABSTRACT

An aspect of the present disclosure includes a composition configured for use in the buccal cavity of a mammal and configured to adhere to the surface of a tooth or teeth and/or one or more orthodontic devices engaged to a tooth. The composition typically includes an admixed composite having an uncured (uncrosslinked) high consistency rubber base material, more typically an uncured (uncrosslinked) silicone high consistency rubber base material; a moisture activated adhesive, typically one or more polyvinylpyrrolidone; and a plasticizer, typically glycerin.

20 Claims, 9 Drawing Sheets

ORTHODONTIC MATERIAL, DEVICE AND METHODS OF PRODUCING THE SAME

CROSS-REFERENCE TO RELATED APPLICATION

This application claims priority to U.S. Provisional Patent Application No. 62/328,973, filed on Apr. 28, 2016, entitled "ORTHODONTIC MATERIAL, DEVICE AND METHODS OF PRODUCING THE SAME," the disclosure of which is hereby incorporated herein by reference in its entirety.

BACKGROUND

Orthodontic brackets and systems are widely used to assist in the straightening or realignment of teeth. The orthodontic brackets are often abrasive against the interior surfaces of one's mouth that has orthodontic braces. Currently there are only a few systems used to prevent abrasion to the interior surfaces of the mouth/wearer caused by braces and other orthodontic device(s) worn in the mouth and all have significant drawbacks. Traditionally, users have mostly used orthodontic relief wax, such as the GUM® brand Orthodontic Wax, to provide protection against abrasion by orthodontic devices; however, this wax is generally provided in small cases and a user repeatedly uses his/her fingers to access the wax, which is potentially unsanitary.

Other solutions to provide protection of the surfaces of a mouth against abrasive surfaces of orthodontic devices such as the use of uncured (uncrosslinked) silicone high consistency rubber alone or uncured (uncrosslinked) silicone high consistency rubber base coated on and present only on the surface with a surface adhesive layer that is an aqueous-based (and subsequently dehydrated) layer of one of a few hygroscopic materials including polyvinylpyrrolidones, starches and gums. Yet other solutions make use of two-part silicone rubber systems that require premixing the parts followed by application to the offending bracket or brackets, followed by a rapid cure during which crosslinking to rubber occurs. Silicone rubbers generally are well known throughout a variety of industries and applications. They are produced in a variety of manners that lead to a cured (crosslinked) $R_2SiO$— polymeric network (R=an organic function such as but not limited to methyl, phenyl, vinyl). Hallmarks of silicone rubber are its hydrophobicity and low surface energy, making adhesion to silicone rubber surfaces a difficult task. It is for this reason that paper is often coated with silicone rubber to serve as a surface from which self-adhering articles such as postage stamps and name tags can be easily removed and applied elsewhere even though they are coated on one surface with a pressure sensitive adhesive. One particular form of crosslinked silicone rubber, known as High Consistency Rubber (HCR), is generated from an uncured (uncrosslinked) silicone HCR base material that consists of one or more silicones, including but not limited to, polydimethylsiloxanes, vinyl-functional polydimethylsiloxanes, silanol-functional polydimethylsiloxanes, Si—H functional polydimethylsiloxanes. The uncured (uncrosslinked) silicone high consistency base material is converted to silicone HCR by inducing curing (crosslinking) by including an appropriate crosslinking catalyst. What differentiates silicone rubber from silicone HCR is that silicone HCR contains an appreciable amount of silica filler mixed into the uncured base material before crosslinking. To achieve a level of silicone polymer and silica filler interaction that provides a stable product while maintaining the reinforcing nature of the filler in the crosslinked elastomer, a treatment, or pacification, of the silanol species on the reinforcing silica filler is necessary. This is typically carried out either through the addition of silanol-end blocked polydimethylsiloxane oligomers or via a capping reaction using reactive silanes or silazanes. Nearly all applications involving silicone HCR uncured (uncrosslinked) base involve its combination with an appropriate cure catalyst (typically peroxides or compounds of platinum) and heating, resulting in crosslinking reactions and a conversion of the silicone HCR uncured base to silicone HCR. There are, however, a few commercial uses of the uncured (uncrosslinked) silicone HCR base such as ear plugs. Another commercial use of uncured (uncrosslinked) silicone HCR base is marketed as OrthoSil™ silicone wax for Orthodontic Patients. Meant to be a superior substitute for traditional hydrocarbon-based orthodontic relief wax to protect the soft tissues of the mouth from irritation and abrasion caused by orthodontic appliances, it has the advantage over wax of being more pliable and comfortable. However, like the traditional hydrocarbon based relief-wax formulations, it has the disadvantage of being unable to adhere to wet teeth and braces due to the hydrophobicity and low surface energy associated with silicones. As a result, the instructions for use of OrthoSil™ recommend well drying of the teeth and brackets to which the OrthoSil™ is to be applied, an often difficult if not virtually impossible task (orthodontic brackets tend to serve as wells for pools of saliva). The instructions state: "Your brackets must be completely dry for silicone wax to adhere properly." Obviously, this is difficult to achieve in the typical conditions of the mouth and given the many surfaces of a typical bracket where saliva gathers.

Another product that uses uncured (uncrosslinked) silicone HCR base is described in US Patent Application Publication No. US 2015/0209120 A1, the disclosure of which is hereby incorporated by reference in its entirety. The uncured (uncrosslinked) silicone HCR base material has a coating of adhesive on its surface to help secure the material onto wet teeth and brackets. The aqueous solution of adhesive is applied to the surface of the uncured (uncrosslinked) silicone HCR base material and then optionally dried. However, this still suffers drawbacks, including the requirement for expensive packaging with appropriate moisture (ambient humidity) barrier to keep the adhesive dry until use, which is not necessary in connection with the material of the present disclosure described herein, and the potential for the user applying the wrong side (the side without adhesive) to the teeth and brackets, in which case it will fail to adhere to wet teeth and braces.

SUMMARY

An aspect of the present disclosure includes a composition configured for use in the buccal cavity of a mammal and configured to adhere to the surface of a tooth and/or one or more orthodontic devices engaged to a tooth. The composition typically includes an admixed homogeneous composite having an uncured (uncrosslinked) high consistency rubber base, more typically a silicone, uncrosslinked high consistency rubber; a moisture activated adhesive, typically polyvinylpyrrolidone; and a plasticizer, typically glycerin.

Another aspect of the present disclosure includes a method of producing an oral medical device, a buccal cavity protection device, and/or treatment device having the steps of: premixing a moisture activated adhesive and a plasticizer to produce a premix; mixing an uncured (uncrosslinked) high consistency rubber composition, more typically a silicone, uncrosslinked high consistency rubber with the premix to produce an admixed composite material, which is typically a homogenous admixed material; optionally mixing one or more active pharmaceutical ingredients into the pre-admixed or admixed composition to form a treatment admixed composite, the mixing may or may not be accompanied by heating; extruding the admixed composite material to produce the buccal cavity protection device or extruding the treatment admixed composite to produce the treatment device.

Yet another aspect of the present disclosure is a kit comprising a plurality of the compositions as disclosed and described herein where the compositions are individually and hygienically packaged and stored in a container that defines the kit. Typically the kit will contain from 2 to 12 compositions that are individually packaged in a single sheet and may be separated by perforations.

Another aspect of the present disclosure is generally directed toward a composition configured for use in the buccal cavity of a mammal that includes: an uncured (uncrosslinked) silicone high consistency rubber base material sized to cover at least a portion or a whole surface of a tooth or teeth with or without an orthodontic device thereon where the uncured (uncrosslinked) silicone high consistency rubber base has a channel thereon; and an elongated bead of a blend of a moisture activated adhesive and a plasticizer spaced within the channel and blended prior to being spaced within the channel.

Yet another aspect of the present disclosure typically includes a method of producing an oral medical device, a buccal cavity protection device, and/or treatment device, the method having the steps of: extruding one or more uncured (uncrosslinked) silicone high consistency rubber base into a band such that the band has a channel along its longitudinal axis; and applying an elongated bead of a blend of a moisture activated adhesive and a plasticizer into the channel. The step of applying the elongated band of the moisture activated adhesive and a plasticizer into the channel is typically done by using a hot melt applicator equipped with a narrow diameter applicator having a diameter less than a width of the channel. Also, the moisture activated adhesive and the plasticizer are typically heated and mixed, typically homogenously mixed, prior to being formed into the bead and applied to the channel.

DETAILED DESCRIPTION

Figure 1A:
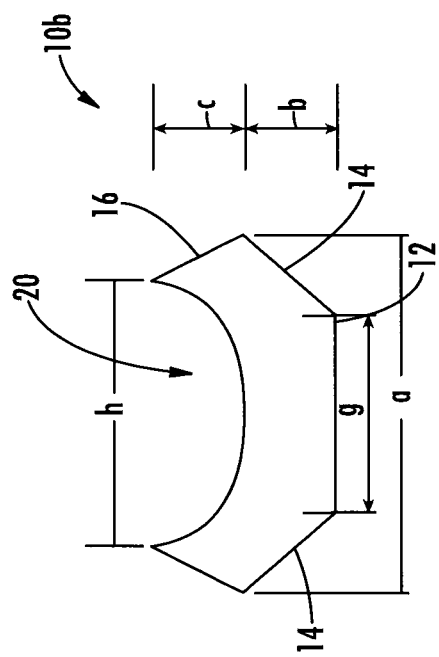
FIG. 1A is a cross-sectional view of an extruded orthodontic protection device of the present disclosure.

Before the subject matter of the present disclosure is described further, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting, instead, the scope of the present disclosure will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

In this specification and the appended claims, the singular forms "a," "an" and "the" include plural reference unless the context clearly dictates otherwise.

Also, as discussed herein tooth means a single tooth and teeth means more than one tooth, but the concepts of the present disclosure and the composites, systems and other disclosed materials of the present disclosure may apply to one or more teeth unless specifically indicated otherwise herein. Tooth is meant to encompass one or more teeth unless indicated otherwise.

The present disclosure is generally directed toward orthodontic protection devices and methods of producing the devices. The uncured (uncrosslinked) silicone high consistency rubber base employed is safe for the oral environment, more pliable than previous compositions, comfortable, and has superior tensile strength, typically the material of the present disclosure tolerates over 30 times more strain without breaking as compared to traditional orthodontic relief wax, based on tensile testing per ASTM D412 guidance compared to GUM® Ortho Wax. The protection devices of the present disclosure adhere to wet teeth and wet brackets or other wet orthodontic devices, however, the devices based on the homogeneous composite in which the adhesive and plasticizer are mixed throughout the uncured (uncrosslinked) silicone HCR base yields at least the following two surprising and novel results:

(1) Even though the adhesive is distributed throughout and therefore coated by the hydrophobic uncured (uncrosslinked) silicone HCR base material, the adhesive still functions and supplies an initial tack to wet teeth and brackets.

(2) Because the adhesive and plasticizer are homogeneously mixed throughout the composite, devices composed of the composite will adhere to wet teeth and wet braces no matter which surface of the material is applied. This gives such devices the tremendous advantage of not being able to be applied in a wrong, non-adhesive manner by the person applying the device.

The materials of the present disclosure enable long term shelf stability via the use of packaging materials with moisture vapor transmission rate values slightly higher, equal to, or lower than thermoformable rigid polyvinylchloride film, with a moisture vapor transmission rate of 2.33 g/m²/day. The material used to form the protection devices of the present disclosure are also able to be impregnated (loaded) with ingredients demonstrated to promote tooth enamel and oral health. Ingredients that may be used and impregnated into the orthodontic material of the present disclosure include, but are not limited to, ingredients/additives that (1) produce fluoride, calcium, and phosphate ions in an aqueous solution and (2) goes on to release such ingredients into the oral environment upon exposure to saliva, which is approximately 99.5% water.

The material used in connection with the present disclosure is a composite comprising uncured (uncrosslinked) silicone HCR base that is thoroughly mixed throughout with one or more polymeric moisture-activated adhesives alone or optionally a combination of one or more polymeric moisture-activated adhesives and one or more compounds that serve to plasticize the adhesives. The uncured (uncrosslinked) silicone HCR base and adhesive are present in a silicone/adhesive weight ratio of from about 7.0 to about 2.0, more typically from about 6.0 to about 3.0, and most typically from about 5.0 to about 4.0.

The homogeneous composite material that forms the typical base material of the orthodontic protection devices of the present disclosure is an uncured (uncrosslinked) silicone HCR base. The uncured (uncrosslinked) silicone HCR base of the present disclosure typically has a water soluble moisture activated adhesive mixed throughout and within the uncrosslinked silicone HCR base, either alone or along with a plasticizer. This combination forms a particularly surprisingly effective device that is capable of adhering to an orthodontic device(s) and/or a surface of a wet (with saliva) tooth. This surprising functionality is counterintuitive because the soft, pliable, moldable silicone HCR base would have been expected to encapsulate the adhesive upon mixing with the adhesive thus rendering the adhesive unable to adhere to wet surfaces.

As will be discussed further below, the inclusion of water soluble compounds into the composite that might serve to release species into saliva known to promote tooth enamel and oral health is also counterintuitive, since water soluble compounds trapped within the extremely hydrophobic silicone HCR base would be expected to be shielded from any external aqueous environment. Nevertheless, the orthodontic protection devices of the present disclosure surprisingly adhere well upon application to the tooth/teeth and/or orthodontic devices of someone wearing orthodontic devices even if the surface the devices of the present disclosure are being applied to is a wet surface or a surface covered with some amount of saliva. The composite adheres well to teeth that are wet with saliva (this includes teeth with and without orthodontic brackets and archwires attached). Additionally, water soluble compounds that produce beneficial effects on and benefits for tooth enamel and oral health may be included in the composite. Quite surprisingly, it has been found that the incorporation of such compounds into the composite base material of the present disclosure do not capture the compounds and contain them within the base material, but rather at least some, typically a beneficial amount capable of having an effect on the teeth are released into the external aqueous environment of the mouth when the composite material is so placed, even if only finger pressure is applied, and the compound is effective for its intended purpose. The force, typically finger pressure, used to apply the composite material to the teeth or braces may typically be from about 0.2 to about 2 pound-force applied by hand and without the use of tools.

Regarding the uncured (uncrosslinked) silicone HCR base material, many companies market uncured (uncrosslinked) silicone HCR base that could be used to prepare composites of the present disclosure, including but not limited to: Wacker Elsatosil R PLUS 4000/50; Wacker Elastosil R 401/50 S; Wacker Elastosil R PLUS 4305/70; Wacker Elastosil R PLUS 4305/60; Wacker Elastosil R plus 4305/80; Wacker Elastosil R 401/80 S; Nusil MED-2174; Nusil MED-4174; Dow Corning Silastic Q7-4535 Medical Grade ETR Elastomer; Dow Corning Silastic Q7-4550 Medical Grade ETR Elastomer; and Dow Corning Silastic Q7-4565 Medical Grade ETR Elastomer.

A variety of polymeric moisture activated adhesives may be used as the polymeric moisture activated adhesive or adhesives that may be mixed into the uncrosslinked silicone HCR base material prior to extrusion and formation of the devices of the present disclosure. Some exemplary polymeric moisture activated adhesives include the following: polyvinylpyrrolidone, polyoxazoline, polyethylene glycols, polyvinyl alcohols, polyacrylic acids, polyacrylamides, polysaccharides (such as xanthan gum, pectins, chitosan derivatives, guar gum, cellulose ethers, starches) and other water-soluble polymeric adhesives or blends of any of the above or other water-soluble polymeric adhesives. One particular polyvinylpyrrolidone that may be used is Plasdone™ K-29/32 polymer, which is a stable, water-soluble polyvinylpyrrolidone that meets U.S., European and Japanese pharmacopoeia specifications for Povidone. This PVP forms complexes with catechins, just as it does with many other compounds that cause discoloration of teeth. The polymer can be used effectively to bind and remove stains through hydrogen bonding with chemical compounds. K-29/32 has the following chemical structure:

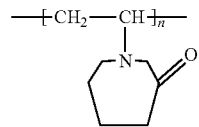

The molecular weight of K-29/32 is about 58,000, it has a K-value of from about 29 to about 32 and a viscosity of about 2.5 mPas in 5% solution. Because of its ability to remove discoloration in teeth, Applicants presently believe that this moisture activated adhesive may also provide the added benefit of stain removal from teeth as well as its primary function of providing the adhesive effect when used in the context of the compositions and composites of the present disclosure.

A variety of compounds that act as plasticizers to the adhesive component may be employed as well along with the moisture activated adhesive(s), including but not limited to: glycerin, any sugar alcohol (such as xylitol, sorbitol, etc.), and polyethylene glycols. One such polyethylene glycol that may be used is polyethylene glycol 400 (PEG 400). If utilized, the plasticizer is typically mixed with the polymeric moisture activated adhesive(s) prior to the combination being admixed into the uncrosslinked silicone HCR base material and thereafter extruded.

In addition, one or more pigment meant to color the silicone HCR base, such as but not limited to, GSDI Silcogum pigments available from POLYONE® can be included into these composites during mixing to achieve practically any color.

In addition, water soluble (to any extent) compounds that produce a variety of benefits to tooth enamel and oral health in general can be included into the composite material and be delivered in an effective amount and manner over a treatment effective period of time. Some of the treatment or benefit inducing compounds that can be included into the composite material include, but are not limited to, the following: sodium fluoride, stannous fluoride, acidulated phosphate fluoride, sodium monofluorophosphate, calcium sulfate, calcium acetate, calcium lactate (with or without addition of xylitol, the combination remineralizes tooth enamel), calcium phosphate, amorphous calcium phosphate complexed with casein phosphopeptides, tricalcium phosphate that has been mechanochemical ball milled with fumaric acid, calcium sulfate, sodium phosphate, potassium phosphate, dipotassium phosphate, and others. Calcium salts and phosphate salts with or without fluoride or carbonate salts may be used. Materials such as calcium chloride, sodium phosphate and sodium fluoride may be placed into non-aqueous mediums and, when they come into contact with saliva, for example, are then re-precipitated as amorphous calcium phosphate, amorphous calcium phosphate fluoride, amorphous calcium carbonate phosphate or amorphous calcium carbonate phosphate fluoride for remineralization of the teeth. The remineralization is further aided by the extended time the composite with the treatment material/components contained therein are applied to the teeth in the context of the present disclosure and their positioning directly around, adjacent and over the braces, which are particular locations where demineralization often occurs when braces are worn. The area around the orthodontic device is particularly treated. Conceivably, the present composite material/system may be used on teeth surfaces or an individual tooth surface that does not have an orthodontic device attached thereto, but rather would be used to apply a delivery method to a tooth for delivery of one or more treatment compositions or compound types whether or not an orthodontic device or devices are present.

Examples of the inventive composites listed below were prepared by first combining adhesive (Ashland Povidone K29/32 polyvinylpyrrolidone powder) with plasticizer (glycerin) via mechanical mixing at room temperature and then heating the mixture in an oven to 160-180° C. in a heavy ceramic mortar to melt it, whereupon uncured (uncrosslinked) silicone HCR base (DOW CORNING® SILASTIC® Q7-4550) was added and heating was continued. The mortar was then removed from the oven and the somewhat now yellowed adhesive was vigorously mixed into the uncured (uncrosslinked) silicone HCR base over the next five to ten minutes as the batch slowly cooled. During the mixing, the mixture transitioned from yellow to white in color as the adhesive was cooling and as the adhesive is dispersed throughout the uncrosslinked (uncured) silicone high consistency rubber base material. Typically the adhesive is at least substantially uniformly or uniformly dispersed throughout the uncrosslinked (uncured) silicone HCR base. Typical batch sizes produced 24 g of composite material on this scale. Batches ranging from 4 to 6 pounds were similarly produced using a Ross heated double planetary mixer equipped with high viscosity blades. Batches ranging up to 33 pounds were similarly produced using a sigma-blade ("Z-blade") mixer. Applicants presently believe that other mixing methods may also be employed such as the use of a two-roll mill, or a SPEEDMIXER™, which is a double rotation of the mixing cup that is sometimes referred to as a dual asymmetric centrifuge. The combination of centrifugal forces acting on different levels in such a device enables very rapid mixing.

The resulting composite was more flexible, pliable, and had greater tensile strength than commercially available orthodontic relief wax. Significantly, as discussed above, the composite, when pressed against wet teeth and braces in any orientation, adhered well to wet teeth and braces and could not be easily removed with just the tongue, but could be removed with purposeful finger gripping and removal force being applied by the fingers. This is in stark contrast to unadulterated uncrosslinked (uncured) silicone HCR base and orthodontic relief wax, neither of which adhere to teeth or braces wet with saliva. The composite also offers the benefit over bits of uncrosslinked (uncured) silicone HCR base that have an adhesive coating applied to the surface in that a piece of the composite of the present disclosure can be applied in any orientation (any of its surfaces) and adhere to wet teeth. Table I lists three composite compositions that adhere to teeth that are wet with saliva.

TABLE I

| Composite Examples | | | |
| --- | --- | --- | --- |
| Composition | Mass Ratio - PVP/glycerin | % Q7-4550 | Additional Fillers |
| A | 1.63 | 75% | NA |
| B | 2.12 | 75% | NA |
| C | 1.69 | 80% | 1.4% |

The Mass Ratio of PVP to glycerin may vary, but would typically range from about 1.0 to about 3.0. Additionally, the weight percent of uncured (uncrosslinked) silicone high consistency rubber base material (Q7-4550) would typically range from about 60 wt. % to about 85 wt. %.

These and all of the inventive composite examples listed below (see Table II below) were easily extruded and cut into any shape and size desired. Possible die shapes include those shown in FIGS. 1A and 1B. Distance "a" in both figures is typically about 7 mm; "b" and "c" are typically both about 2 mm; "d" is about 1.5 mm; "e" is about 3 mm; "f" is about 1.5 mm; "g" is about 4 mm and "h" is about 6 mm. The shapes 10a and 10b produced typically have a base 12 on upwardly extending first portion 14 and second portion 16 that are each at an acute angle 18 to one another. The shapes 10a, 10b typically define a orthodontic device (bracket) receiving recess or, in the case of a strip, a channel having an interior volume 20 defined at least by the base and sides. Composite material may be extruded at ambient temperature through a 6 mm×3 mm rectangular die and cut into 6 mm lengths to achieve bits of composite meant to be applied to a single bracket causing irritation in the mouth or oral mucosal tears. Composite was also extruded at ambient temperature through either of the dies shown in FIG. 1A or 1B and cut into various lengths to produce strips meant to cover multiple brackets (trapezoidal groove (FIG. 1A) and curved "bowl" groove (FIG. 1B) pressed against teeth and brackets). These systems may be used to prevent or lessen wound development caused by the orthodontic devices in the oral cavity; may be used to prevent or lessen the risk of wound development during sports activities; may be used to prevent or lessen the risk of wound development during the playing of musical wind instruments; may be used to administer one or more actives or treatment compositions used to treat teeth typically the enamel of the teeth, including but not limited to, the treatment, prevention or lessening of hypomineralization. Applicants presently believe that the composites of the present disclosure may be used to remineralize the enamel when appropriate treatment compositions are included in (blended into) the composite material.

The shapes and sizes described for small bits and longer strips of composite for application to the teeth and braces are meant only as examples, and are in no way meant to be limiting, nor is extrusion the only method that could be used to produce desired devices from the inventive composite. Other methods including, but not limited to, molds and/or two roll mills or presses to produce flat sheets followed by cutting may also be used.

The following are examples of composites of the present disclosure including some that contain water soluble compounds that produce species of benefit to tooth enamel and oral health. These examples are in no way meant to be limiting, but simply illustrate the possibilities. All were prepared as described above, with the modification that compounds that produce species of benefit to tooth enamel and oral health were incorporated into the composite via addition to and mixing throughout the polyvinylpyrrolidone powder before addition of the glycerin.

Prior drying of the bracket and tooth surface to which the composite was applied was found to not be necessary to obtain good adhesion. Furthermore, pieces of composite could be successfully applied with a simple push and pinch using fingers to apply the composite onto a bracket lasting where the push and pinch force lasts no more than three seconds, more typically no more than one second, with no failure to adhere. The composite is able to be left on for 24 hours or more with the wearer being able to eat and drink during that time period with the composite not falling off unless purposefully removed. The pieces of composite remained malleable, soft, and comfortable, and remediated the source of irritation during the wear time.

In addition to composite pieces, the composite may be made into strips. The strips may protect against injury as discussed above from orthodontic devices such as braces, brackets and archwires. The strips may be used for protection while playing a sport or undertaking another activity where the user is actively moving about and/or where it is possible a ball or other projectile may hit a user's mouth and apply a force to the outside of the wearers mouth that thereby forces the soft tissue of the lip(s) or mouth into contact with the orthodontic devices of the wearer. The strips significantly cushion against such a force. Therefore, not only are the strips a shield against frictional force and a potential delivery device for one or more actives or treatment compositions, but the strips may also lessen or prevent potential injury from impact forces. Multiple 1⅞" length and multiple 2¼" length strips extruded with the dies shown in FIGS. 1A and 1B were made from composite of Examples 3 and 4. Strips so made are easy to apply and adhere well. The strips stay on without failure for at least 4-5 hours but

TABLE II

Composite Examples

| Example | % Q7-4550 | % PVP | % Glycerin | % NaF | % CaSO$_4$ | % Ca(OAc)$_2$* | % K$_2$HPO$_4$ |
|---|---|---|---|---|---|---|---|
| 1 | 75.0 | 15.5 | 9.50 | — | — | — | — |
| 2 | 80.0 | 12.8 | 7.20 | — | — | — | — |
| 3 | 75.0 | 14.6 | 8.60 | 1.25 | 0.25 | — | 0.29 |
| 4 | 79.9 | 11.7 | 6.95 | 1.03 | — | 0.20 | 0.20 |

*OAc is acetate, CH$_3$COO$^-$

Example 3 and Example 4 have the following makeup prior to being added to the HCR base material.

Example 3

58.4% PVP
1.0% CaSO$_4$
1.0% K2HPO$_4$
5% NaF
34.6% glycerin

The composite was 25% by mass of the above formulation blended into 75% Q7-4550 uncured (uncrosslinked) silicone HCR base.

Example 4

58.4% PVP
1.0% Ca(OAc)$_2$.2H$_2$O
1.0% K2HPO$_4$
5% NaF
34.6% glycerin

The composite was 20% by mass of this formulation blended into 80% Q7-4550 uncured (uncrosslinked) silicone HCR base.

up to 24 hours. The strips may be removed easily at the end of any period of use and leave little to zero noticeable residue on the teeth and braces or other orthodontic devices of the wearer.

Figure 1B:
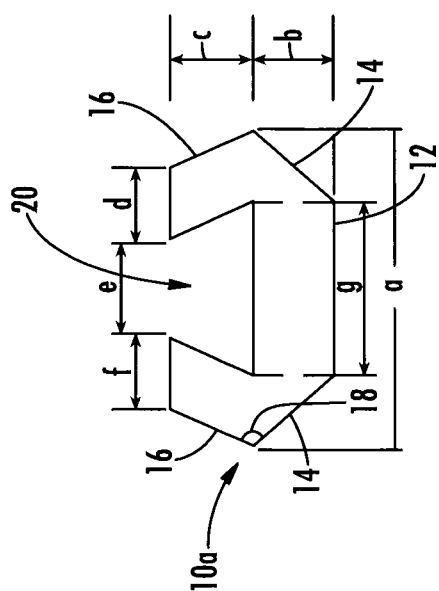
FIG. 1B is a cross-sectional view of another extruded orthodontic protection device of the present disclosure.

Strips composed of Example 3 (calcium sulfate as the calcium source) and Example 4 (calcium acetate as the calcium source) composite, extruded from the die shown in FIGS. 1A and 1B, were placed in stirred reverse osmosis (RO) water maintained at 37° C., and fluoride ion, calcium ion, and phosphate ion concentrations were measured over time using a Extech FL-700 fluoride selective electrode, a Pinpoint II calcium monitor (calcium selective electrode), and a Hanna Phosphate meter (colorimetric phosphate determination), respectively. Data collected was used to generate the release curves shown in FIGS. 2-7 (mcg=micrograms).

These release curves clearly show that fluoride ions, calcium ions, and phosphate species, all recognized as promoting tooth enamel and oral health, are leachable and enter aqueous solution from strips composed of the composites of the present disclosure by water at the temperature of the human mouth. The curves also teach that the rates at which actives are released are, in part, a function of the aqueous solubility of the compounds that are the source of these ions. For example, $CaSO_4$ is much less soluble in water than $Ca(OAc)_2$, resulting in an 81.8% release of calcium ions after 4 hours by an Example 4 strip compared to an only 51.9% release of calcium ions after 25 hours by an Example 3 strip.

Figure 2:
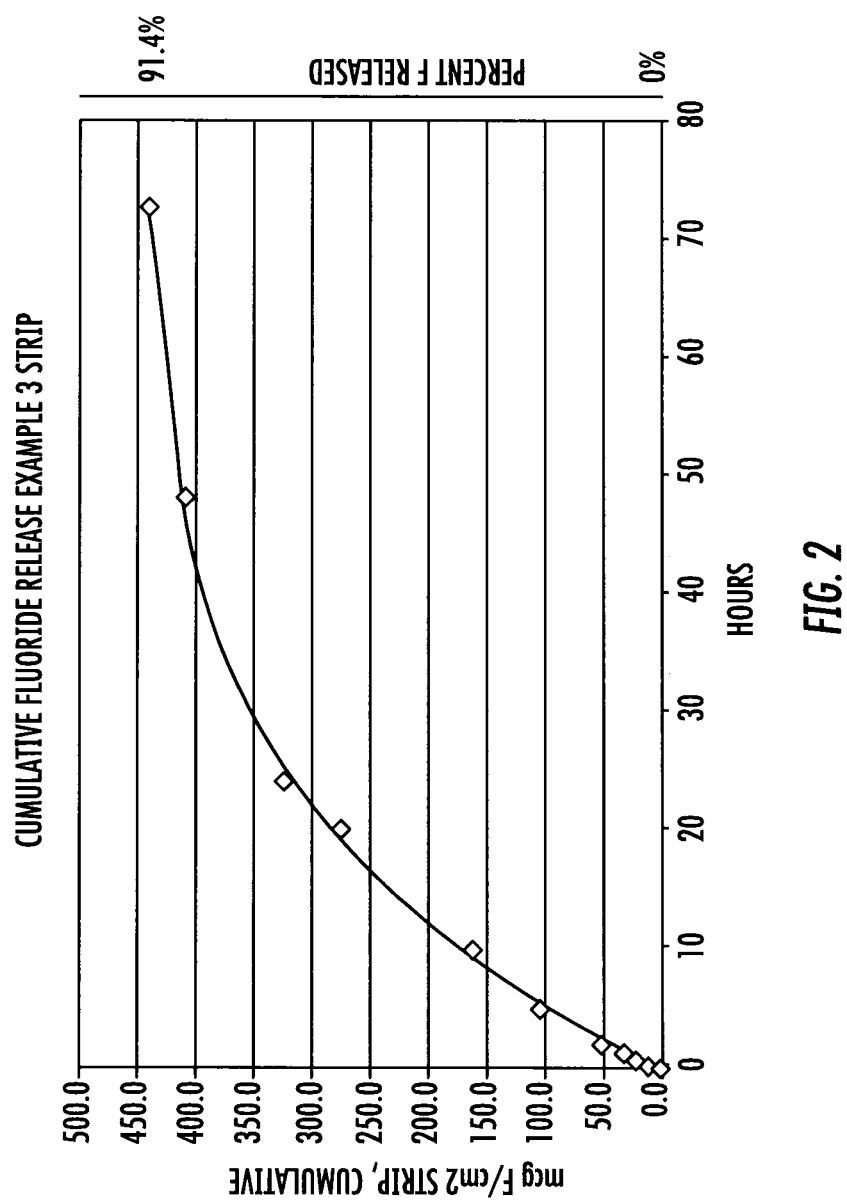
FIG. 2 is a cumulative fluoride release profile for the strip product according to an embodiment of the present disclosure described in Example 3 incorporating sodium fluoride as the fluoride source.
Figure 3:
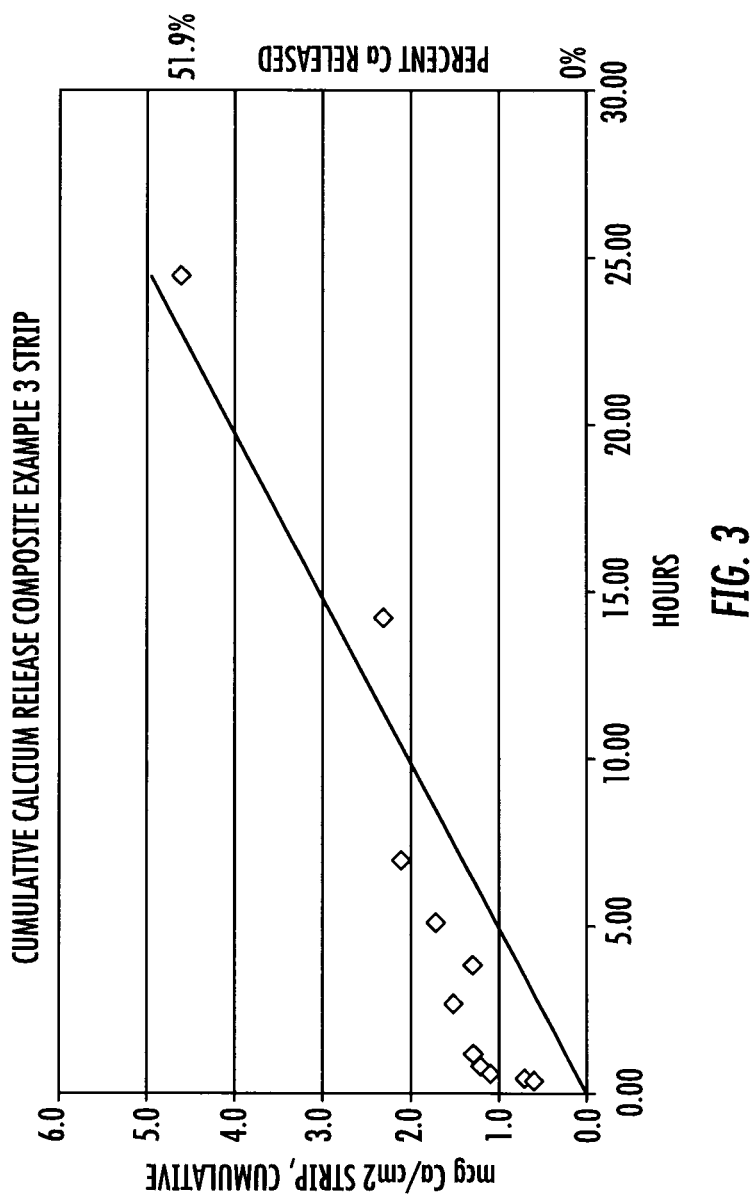
FIG. 3 is a cumulative calcium release profile for the strip product according to an embodiment of the present disclosure described in Example 3 incorporating calcium sulfate as the calcium source.
Figure 4:
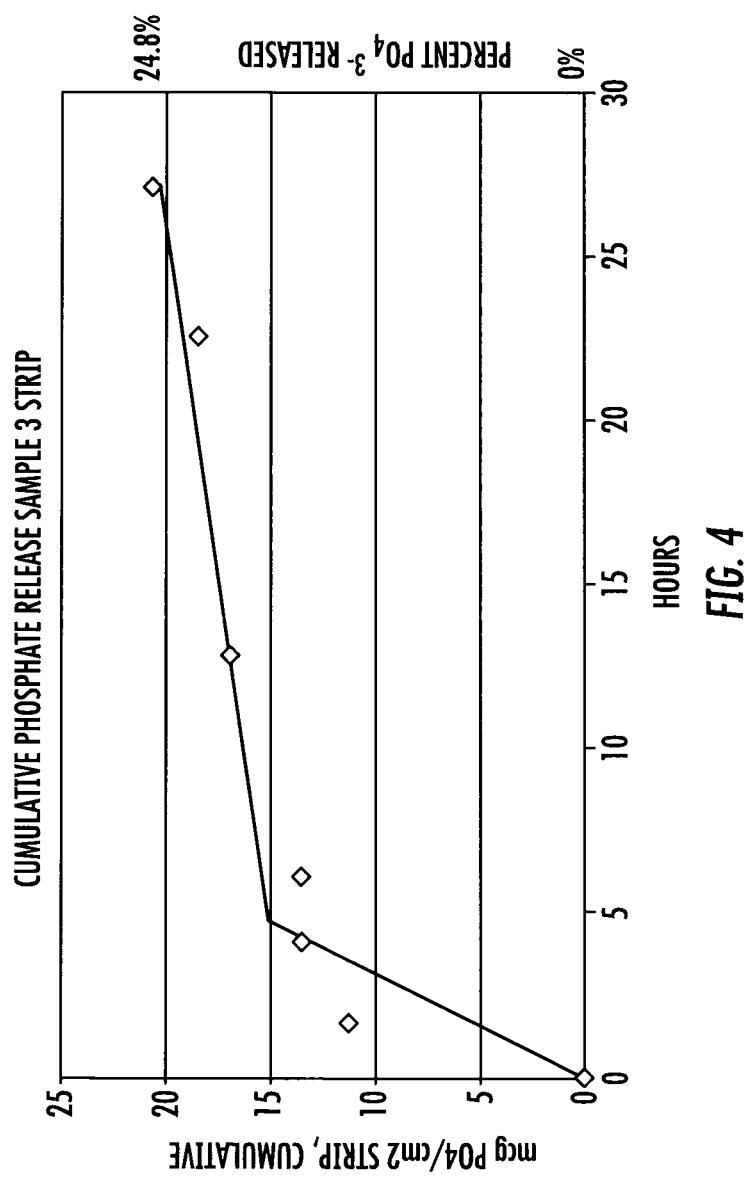
FIG. 4 is a cumulative phosphate release profile for the strip product according to an embodiment of the present disclosure described in Example 3 incorporating dipotassium phosphate as the phosphate source.

Again, as shown in FIGS. 2-7, the various one or more active materials release over time and in greater amounts than prior systems such as varnishes currently used in the art. In the case of FIG. 2, this shows the cumulative release of fluoride (1.25% NaF; 0.2% $CaSO_4$; 0.3% $K2HPO_4$). At 4 hours, 17.9% (1.0 mg) was released and at 24 hours, 67.7% (3.8 mg) was released. The strip of this Example contains 5.6 mg fluoride (11,360 ppm fluoride). FIG. 3 shows the cumulative calcium release from the composite media. As shown in FIG. 3, the calcium release from the Example strip containing 1.25% NaF; 0.2% $CaSO_4$; 0.3% $K_2HPO_4$ ranged from about 48 ppm to about 112 ppm. The release profile of phosphate from the Example strip containing 1.25% NaF; 0.2% $CaSO_4$; 0.3% $K_2HPO_4$ is shown in FIG. 4.

Figure 5:
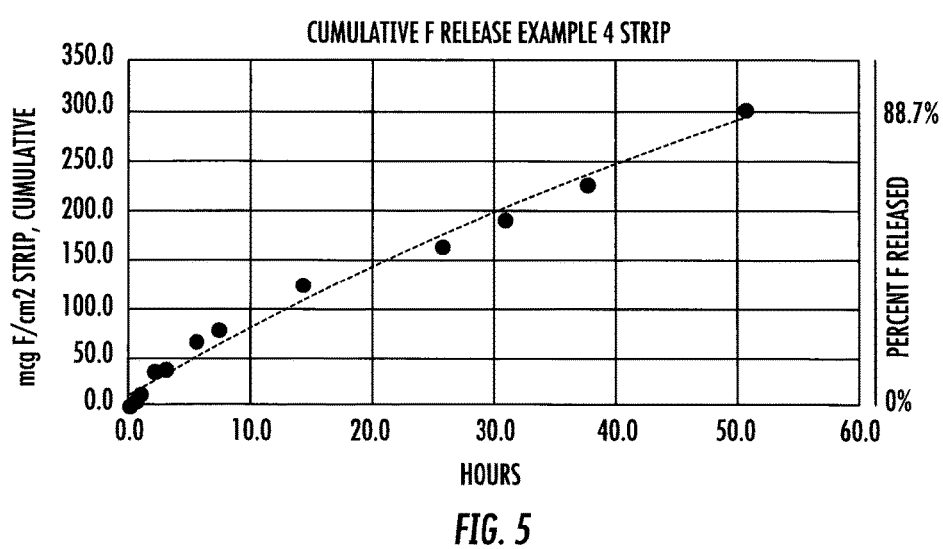
FIG. 5 is a cumulative fluoride release profile for the strip product according to an embodiment of the present disclosure described in Example 4 incorporating sodium fluoride as the fluoride source.
Figure 6:
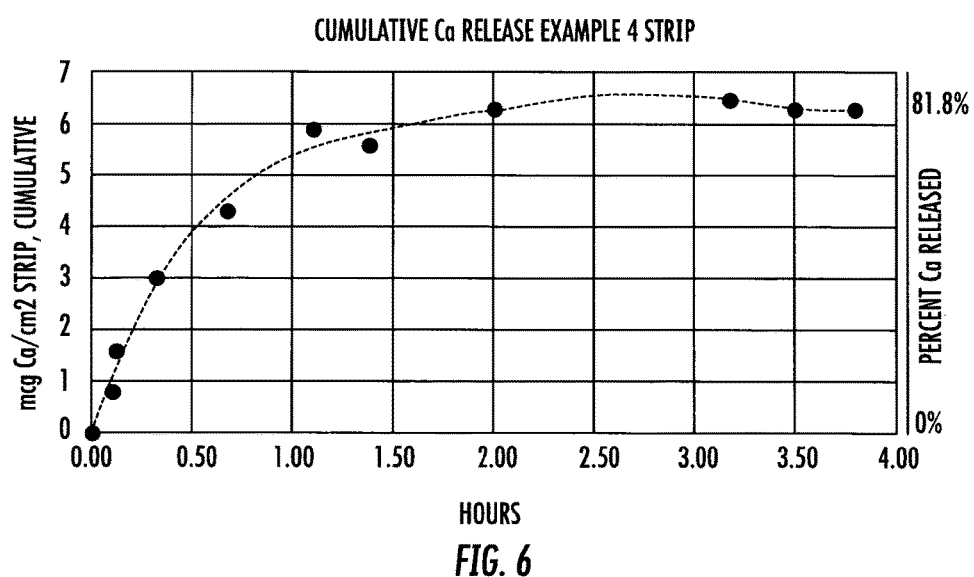
FIG. 6 is a cumulative calcium release profile for the strip product according to an embodiment of the present disclosure described in Example 4 incorporating calcium acetate as the calcium source.
Figure 7:
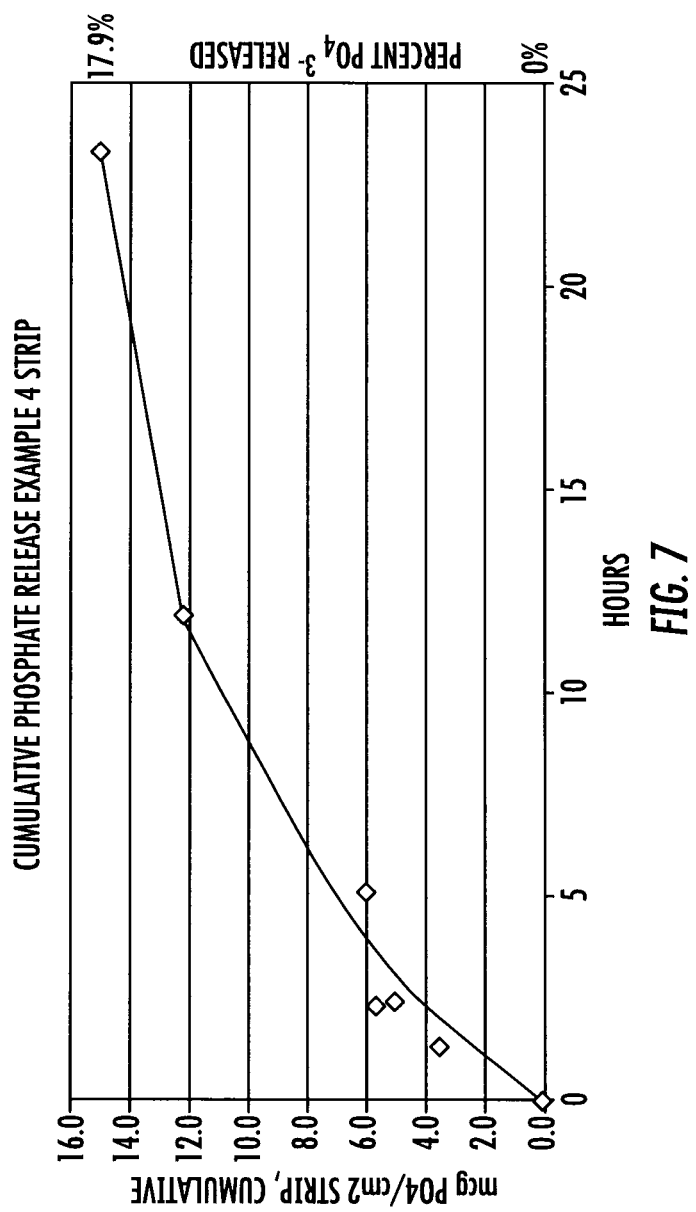
FIG. 7 is a cumulative phosphate release profile for the strip product according to an embodiment of the present disclosure described in Example 4 incorporating dipotassium phosphate as the phosphate source.

FIGS. 5-7 show the release profile for a composite material containing 1.0% NaF; 0.2% $Ca(OAc)_2$; 0.2% $K_2HPO_4$. Calcium acetate is more soluble than calcium sulfate, which is evident in this formulation. As shown in FIG. 6, the release profile shows a calcium in saliva ranging from about 48 to about 112 ppm. The release profile for fluoride from this composite is shown in FIG. 5 and the release profile for phosphate from this system is shown in FIG. 7.

Figure 8:
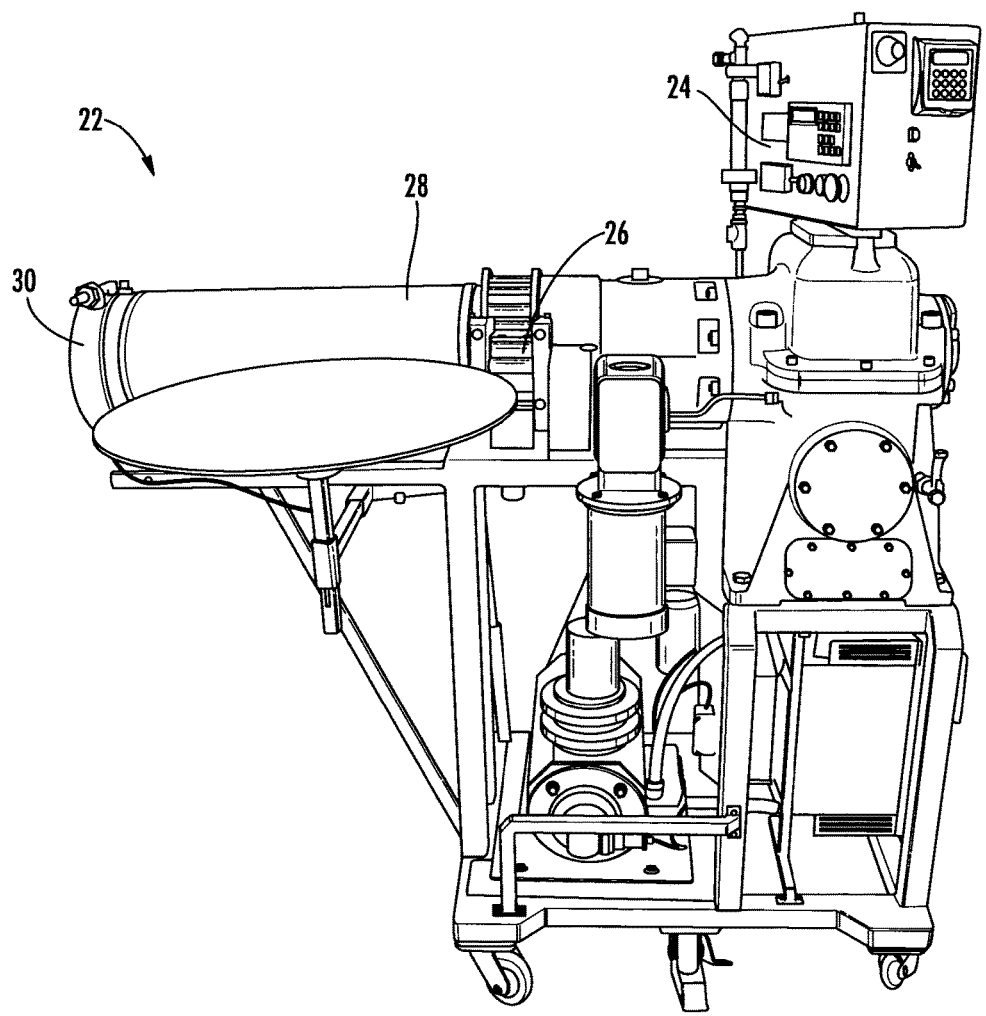
FIG. 8 is a perspective view of a DAVIS™ three inch single screw medical grade extruder used to extrude the composite materials of the present disclosure.

While not as preferred as the composite material, Applicants also believe that the uncured (uncrosslinked) silicone HCR base material may be used and extruded into strips. In this alternate embodiment, the extruded strips would be extruded such that there would be a groove longitudinally along the strip or portion of material extruded as it is extruded. Two particular possible extruded grooves or channels include those produced when one of the extrusion dies shown in FIGS. 1A and 1B are used. Basically, looking in the cross section, the top transverse surface of the strip has a groove or channel internal volume 20. The groove or channel internal volume 20 may be filled with an aqueous-based gel formulation that may or may not have one or more of the treatment compounds discussed above mixed therein. Typically the extruder used is a DAVIS™ three inch single screw medical grade extruder as shown in FIG. 8. The extruder 22 has a control bond 24, a roll feeder 26, a single extrusion screw 28, and an extrusion die 30.

A simple dispenser such as a pipette may be used to apply a bead of aqueous adhesive into the groove or channel interior volume 20 of the extruded composite material. Typically the aqueous adhesive is added to the groove or channel shortly after the uncured (uncrosslinked) silicone high consistency rubber base material is extruded, but the adhesive may be added after a period of time or further down a line of a manufacturing process. The adhesive formulation may include one or more actives such as fluoride. The filled strips are then baked in an oven (typically at about 120° C.) for a sufficient time (typically from about 4 hours to about 8 hours) to drive off the majority of the moisture from the groove-filling formulation, leaving behind a semi-solid gel.

When an aqueous formulation is formed it may be formed on an experimental scale by combining in a 600 ml beaker, 64.51 g reverse osmosis water, 17.40 g of polyvinylpyrrolidone powder (PVP, Ashland Plasdone K29/32), 17.40 g glycerin, 0.504 g xanthan gum, 0.089 g NaF, and optionally four drops of a colorant such as Blue #1 food coloring solution (available from GORDON FOOD SERVICE® of Grand Rapids, Mich.). This was stirred at 300 rpm with a stainless steel paddle stirrer until the mixture was homogenous and had thickened a bit. A pipette was then used to completely fill the grooves of the extruded strips and the strips were then placed into a 120° C. oven for approximately 4.5 hours. The resulting gel was pliable and allowed for easy application to orthodontic braces, effectively affixing the device to the teeth and braces, and allowing for the gel to slowly dissolve into the saliva over a period of at least 8 hours. The aqueous adhesive formulation may include fluoride and phosphate, but calcium cannot be added, because in aqueous solution, either calcium fluoride or calcium phosphate will precipitate, taking all the actives out of solution and making them ineffective.

One Exemplary aqueous gel that may be employed was the following composition (amounts are percent by weight):
64.5% water
17.5% PVP
17.5% Glycerin
0.5% Xanthan Gum In other examples, some amount of water may be removed and one or more active added. For example from about 0.01% to about 0.1% by weight sodium fluoride (NaF) may be added. $CaSO_4$ or $Ca(OAc)_2$ (calcium acetate) and/or $K_2HPO_4$ at no more than 2% by weight each may be added in place of some water.

Figure 9:
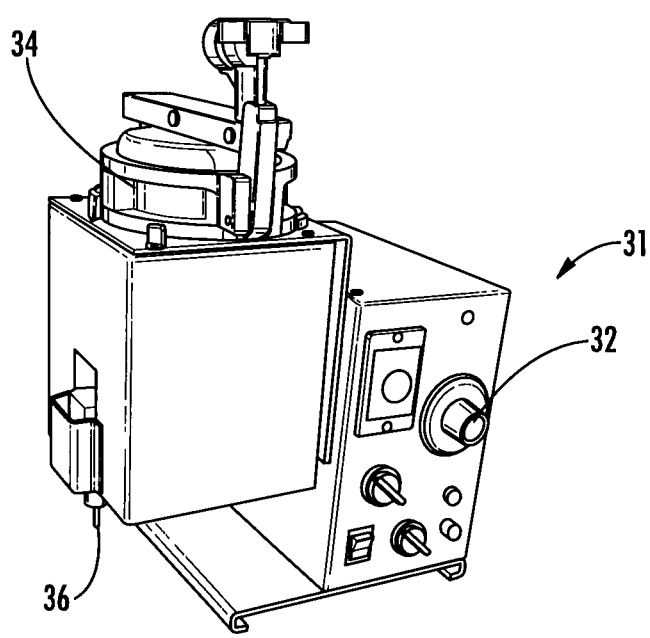
FIG. 9 is a perspective view of a SUREBONDER® 753 Pneumatic Hot Glue Dispenser.

Alternatively to an aqueous based system that might be used to fill the groove or channel, a non-aqueous adhesive formulation that includes one or more actives may be used in the composite and be admixed therein. In particular, one such set of additive compounds include: sodium fluoride, calcium sulfate, and dipotassium phosphate. To form this non-aqueous adhesive system to be extruded and applied into the channel/groove in experimental amounts the following process may be used. 60.0 g of polyvinylpyrrolidone powder (PVP, Ashland Plasdone K29/32), 35.76 g glycerin, 2.0 g $CaSO_4$, 2.0 g $K_2HPO_4$, and 0.24 g NaF were mixed with a stainless steel spatula by hand in a beaker and then transferred into the tank of a SUREBONDER® 753 Pneumatic Hot Melt Applicator equipped with narrow diameter applicator tip. FIG. 9 is a perspective view of a SUREBONDER® 753 Pneumatic Hot Glue Dispenser 31, which may be used in connection with this embodiment of the present disclosure to apply the non-aqueous adhesive into the channel or groove of the extruded strips. The glue dispenser 31 includes a temperature control knob 32, an adhesive tank 34 and a dispenser tip 36.

When forming the non-aqueous mixture according to this example, the applicator was set to 170° C. to melt the adhesive formulation with additional stirring, whereupon the applicator was used to fill the grooves of the above-described strips to various extents. The resulting glycerin-plasticized adhesive was pliable and allowed for easy application to orthodontic braces, effectively affixing the device to the teeth and braces, and allowing for the adhesive formulation to slowly dissolve into the saliva over a period of at least 8 hours. As mentioned above, the aqueous formulation can include fluoride or fluoride+phosphate, but calcium cannot be added, because in aqueous solution, either calcium fluoride or calcium phosphate will precipitate, taking all the actives out of solution and making them ineffective. The hot melt method and use of a non-aqueous adhesive system avoids any water, so even though all of the sources of fluoride, calcium, and phosphate are present in the same formulation, without the water, they cannot dissolve for calcium ions to react with fluoride and phosphate. When saliva hits the non-aqueous adhesive solution, then these ions will be released.

The composite strips or the strips with the adhesive applied as a bead of material within a groove or channel in a base material deliver fluoride at over the counter or professional strength, deliver calcium and phosphate, may be applied with finger pressure and force, can be worn on braces or other orthodontic devices while eating or drinking, but can be removed at will without brushing. The systems of the present disclosure provide relief from irritation and abrasion, requires no premixing or application tools and may be applied in about 5 seconds or less, or more typically about 10 seconds or less.

What is claimed is:

1. A composition configured for use in a buccal cavity of a mammal comprising:
   a composite material that is safe for use in the buccal cavity of the mammal comprising a moisture activated adhesive and a plasticizer at least substantially uniformly dispersed throughout an uncured, uncrosslinked high consistency rubber base material.

2. The composition of claim 1, wherein the composite material is at least substantially free of water.

3. The composition of claim 2, wherein the composite material is a non-aqueous composite and the moisture activated adhesive and the plasticizer are uniformly dispersed throughout the uncured, uncrosslinked high consistency rubber base material.

4. The composition of claim 1, wherein the plasticizer is a water soluble plasticizer and the water soluble plasticizer is present in an amount of from about 2% by weight to about 25% by weight of the composite material.

5. The composition of claim 1, wherein the moisture activated adhesive is a water-soluble polymeric adhesive or a blend of water-soluble polymeric adhesives.

6. The composition of claim 2, wherein the moisture activated adhesive is chosen from the group consisting of a polyvinylpyrrolidone, a polyacrylic acid, a polysaccharide, and mixtures thereof and wherein the composition is a shaped composition having an interior orthodontic bracket receiving recess on a surface of the shaped composition.

7. The composition of claim 6, wherein the moisture activated adhesive consists of one or more polyvinylpyrrolidone.

8. The composition of claim 6, wherein the plasticizer is glycerin and the glycerin and the moisture activated adhesive are mixed into a premixture and thereafter at least substantially uniformly dispersed throughout the uncured, uncrosslinked high consistency rubber to form the composite material.

9. The composition of claim 1, wherein the composite material is configured to adhere with finger pressure to a moist surface of at least one tooth.

10. The composition of claim 1, wherein the composite material is configured to adhere with finger pressure and finger force of up to 2 pound force to an exterior facing surface of a moist orthodontic appliance affixed to a tooth in the buccal cavity of a mammal.

11. The composition of claim 1, wherein the moisture activated adhesive is a polyvinylpyrrolidone powder that forms complexes with catechins.

12. The composition of claim 1, wherein the composite material further comprises one or more agents to support healthy teeth or whiten teeth wherein the one or more agent to support healthy teeth or whiten teeth is present in the composite material in an amount of from about 0% by weight to about 10% by weight of the composite material.

13. The composition of claim 12, wherein the one or more agents to support healthy teeth or whiten teeth are chosen from the group consisting of: sodium fluoride, stannous fluoride, acidulated phosphate fluoride, sodium monofluorophosphate, calcium sulfate, calcium acetate, calcium lactate, calcium phosphate, amorphous calcium phosphate complexed with casein phosphopeptides, tricalcium phosphate that has been mechanochemical ball milled with fumaric acid, sodium phosphate, potassium phosphate, dipotassium phosphate, and mixtures thereof and wherein the composite material further comprises a colorant or pigment; and wherein the one or more agents to support healthy teeth or whiten teeth are at least substantially uniformly dispersed or uniformly dispersed throughout the uncured, uncrosslinked high consistency rubber base material.

14. The composition of claim 12, wherein the one or more agents are capable of preventing or slowing demineralization of enamel of a tooth; and wherein the one or more agents to support healthy teeth or whiten teeth are at least substantially uniformly dispersed or uniformly dispersed throughout the uncured, uncrosslinked high consistency rubber base material.

15. The composition of claim 1, wherein the composite material comprises from about 50% to about 95% by weight uncured, uncrosslinked high consistency rubber base material and the uncured, uncrosslinked high consistency rubber base material is a silicone, uncured, uncrosslinked high consistency rubber base material.

16. The composition of claim 15, wherein the composite material comprises from about 60% to about 85% by weight uncured, uncrosslinked silicone high consistency rubber base material.

17. The composition of claim 16, wherein the composite material comprises from about 70% to about 80% by weight uncured, uncrosslinked silicone high consistency rubber base material.

18. The composition of claim 1, wherein the moisture activated adhesive is a water soluble adhesive polymer and the water soluble adhesive polymer is present in the composite material in an amount of from about 5% by weight to about 80% by weight of the composite material.

19. The composition of claim 1, wherein the composition is a shaped composition having a base, at least two upwardly extending side walls and an interior, orthodontic device receiving cavity where the shaped composition is:
   (1) sized to be placed on a single tooth, and over an orthodontic device on a facial surface of the single tooth where the orthodontic device is received in the interior, orthodontic device receiving cavity; or
   (2) sized to be placed on a plurality of adjacent teeth where the plurality of the adjacent teeth have an orthodontic device on the facial surface of the adjacent teeth and the interior, orthodontic device receiving cavity is a channel.

20. A composition configured for use in a buccal cavity of a mammal comprising:
   an admixed, non-aqueous composite material that is safe for use in the buccal cavity of the mammal comprising:
   an uncured, uncrosslinked high consistency rubber base material;
   a moisture activated adhesive chosen from the group consisting of a polyvinylpyrrolidone, polyoxazoline, a polyethylene glycol, a polyvinyl alcohol, a polyacrylic acid, a polyacrylamide, a polysaccharide, and mixtures thereof; and
   a plasticizer that is a water soluble plasticizer and the water soluble plasticizer is present in an amount of from about 2% by weight to about 25% by weight of the composite material; and wherein the moisture activated adhesive and the plasticizer are dispersed within the admixed, non-aqueous composite material.

* * * * *